(12) United States Patent
Ahmad et al.

(10) Patent No.: US 7,786,055 B2
(45) Date of Patent: Aug. 31, 2010

(54) ANTIOXIDANT COMPOSITIONS FOR REDUCING ODOR IN WARMING LUBRICANT COMPOSITIONS

(75) Inventors: Nawaz Ahmad, Monmouth Junction, NJ (US); Cheng-Ji Cui, Pennington, NJ (US); Vinayak Santayya Kamat, Hillsborough, NJ (US); Shirley Ng, Bridgewater, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 535 days.

(21) Appl. No.: 11/403,592

(22) Filed: Apr. 13, 2006

(65) Prior Publication Data
US 2007/0243219 A1 Oct. 18, 2007

(51) Int. Cl.
*C10M 177/00* (2006.01)
*C10M 704/24* (2006.01)
*C10M 129/10* (2006.01)
*A61K 9/00* (2006.01)

(52) U.S. Cl. .................. 508/110; 508/304; 508/577; 508/583; 424/401

(58) Field of Classification Search ................ 508/577, 508/578, 579, 580, 583, 584, 587
See application file for complete search history.

(56) References Cited

U.S. PATENT DOCUMENTS

| 2003/0170198 | A1 | 9/2003 | Williams |
| 2003/0211173 | A1 | 11/2003 | Veach et al. |
| 2005/0042248 | A1* | 2/2005 | Ahmad et al. ............... 424/423 |
| 2005/0260253 | A1* | 11/2005 | Leonardi et al. ............ 424/448 |

FOREIGN PATENT DOCUMENTS

| JP | 04154726 A | 5/1992 |
| WO | WO 00/45795 A | 8/2000 |
| WO | WO 03/092652 A | 11/2003 |
| WO | WO 2005/035011 A | 4/2005 |

* cited by examiner

*Primary Examiner*—Glenn A Caldarola
*Assistant Examiner*—Taiwo Oladapo

(57) ABSTRACT

This invention relates to the clear, substantially anhydrous, warming compositions containing one or more polyhydric alcohols. The invention also relates to the compositions that include at least one or more antioxidant or antioxidants in combination selected from the group consisting of tocopherol, ascorbic acid and butylated hydroxytoluene (BHT), to prevent oxidation of polyhydric alcohol combination that results in the development of odor.

13 Claims, No Drawings

ANTIOXIDANT COMPOSITIONS FOR REDUCING ODOR IN WARMING LUBRICANT COMPOSITIONS

FIELD OF THE INVENTION

This invention relates to personal lubricant compositions that are warming and nonirritating when applied to the skin or mucous membranes, especially the vaginal or oral mucosa. The compositions of this invention are substantially anhydrous and contain one or more polyhydric alcohol. This invention also relates to the compositions that include at least one or more antioxidant or antioxidants in combination, to prevent oxidation of polyhydric alcohol combination that results in the development of odor.

BACKGROUND OF THE INVENTION

Warming personal lubricants and medicament compositions have been relatively recently introduced into the market. Such warming personal lubricants are described in, for example, U.S. Pat. No. 7,005,408 as well as in U.S. patent application Ser. No. 10/390,511 filed Mar. 17, 2003, Ser. No. 10/389,871, filed Mar. 17, 2003, Ser. No. 10/696,939, filed Oct. 30, 2003, Ser. No. 10/697,353, filed Oct. 30, 2003, Ser. No. 10/697,838, Oct. 30, 2003, Ser. No. 10/847,082, May 17, 2004 and Ser. No. 10/847,083, filed May 17, 2004, which are hereby incorporated herein by reference. Although personal lubricants and related compositions made in accordance with the foregoing patent and applications have been utilized extensively, they have been discovered to develop offensive odors under certain circumstances. The offensive odor may be present due to elevated temperatures during storage.

Thus, there is a need to develop means for substantially preventing or remediating offensive odor produced in conjunction with warming personal lubricants.

SUMMARY OF THE INVENTION

The invention relates to a substantially anhydrous lubricant composition comprising at least one polyhydric alcohol, a bioadhesive agent and at least one antioxidant selected from a particular group of antioxidant compounds. Surprisingly, and contrary to the general belief that all antioxidants would substantially prevent the formation of offensive odors in compositions that include polyhydric alcohols, we have found that only certain antioxidants are suitable for preventing such odors. Polyhydric alcohols that may be preferably included in the compositions of this invention are propylene glycol or a polyethylene glycol. The antioxidants that are useful in the substantial mediation of odor formation are preferably selected from a group consisting of butylated hydroxytoluene (BHT), ascorbic acid and tocopherol. Compositions of this invention are similar to the compositions described in, for example, U.S. Pat. No. 7,005,408, incorporated herein by reference.

The combination of polyhydric alcohols and select antioxidants in the compositions of this invention may also be used as a vehicle to solubilize otherwise insoluble drugs, including, but not limited to, antifungals, antibacterials, antivirals, analgesics, anti-inflammatory steroids, contraceptives, local anaesthetics, hormones and the like.

The compositions of this invention also preferably contain an insulating agent which functions to preserve the temperature increase by maintaining the heat within the composition after it has been applied to the skin or mucosa. More preferably, honey may be present in the compositions of this invention.

DETAILED DESCRIPTION OF THE INVENTION

The compositions of this invention are substantially anhydrous, preferably containing less than about 20% water, more preferably containing less than about 5% water and, most preferably, containing less than about 3% water. Preferably, the compositions of this invention contain at least one antioxidant. Preferably the antioxidant portion of the composition has at least one antioxidant such as butylated hydroxytoluene (BHT), ascorbic acid, tocopherol and propyl gallate. The compositions of this invention should contain antioxidants in an amount from about 0.01% to about 0.5% by weight of the composition.

Preferably, the compositions of this invention contain at least one polyol. Preferably, the polyol is a polyhydric alcohol, and more preferably, at least two polyhydric alcohols. Polyethylene glycol (hereinafter, "PEG") ethers may also be used, including PEG ethers of propylene glycol, propylene glycol stearate, propylene glycol oleate and propylene glycol cocoate and the like. Specific examples of such PEG ethers include PEG-25 propylene glycol stearate, PEG-55 propylene glycol oleate and the like. Preferably, at least one of the polyhydric alcohols of the compositions of this invention is a polyalkylene glycols or others selected from the following group: glycerine, propylene glycol, butylene glycol, hexalene glycol or polyethylene glycol of various molecular weight and the like and/or combination thereof. More preferably, the compositions of this invention contain a polyethylene glycol; most preferably, the polyethylene glycol may be selected from the following group: polyethylene glycol 400 or polyethylene glycol 300. Polypropylene glycol of various molecular weights may also be used. PEGylated compounds such as peptide or protein derivatives obtained through PEGylation reactions may also be used. In addition, block copolymers of PEG's may be used, such as (ethylene glycol)-block-poly(propylene glycol)-block-(polyethylene glycol), poly(ethylene glycol-ran-propylene glycol) and the like. The compositions of this invention should contain polyhydric alcohols in an amount from about 80% to about 98% by weight of the composition.

Preferably, the compositions of this invention contain at least one polyhydric alcohol, and more preferably, at least two polyhydric alcohols. Preferably the polyhydric alcohol portion of the compositions of this invention one or more polyhydric alcohols such as alkylene glycols and others selected from the following group: glycerin, propylene glycol, butylene glycol, hexalene glycol or polyethylene glycol of various molecular weight and the like and/or combination thereof. More preferably, the compositions of this invention contain a polyethylene glycol; most preferably, the polyethylene glycol may be selected from the following group: polyethylene glycol 400 or polyethylene glycol 300. The compositions of this invention should contain polyhydric alcohols in an amount from about 80% to about 98% by weight of the composition.

The compositions of this invention preferably also contain an insulating agent. More preferably, the insulating agent should be honey or esters of isopropyl alcohol and saturated high molecular weight fatty acids such as myristic or palmitic acid, e.g., isopropyl myristate and isopropyl palmitate. The insulating agent should be present in the compositions of this invention in an amount of from about 1% to about 5% by weight of the composition.

We theorize that, when the polyhydric alcohols contained in the compositions of this invention come into contact with water or body moisture in humans, they react with the ambient water molecules to cause an increase in temperature or generate warmth, thus having a soothing effect on the tissues to which these compositions are applied. We also theorize that when these compositions are stored for a period of time at elevated temperatures they develop an offensive odor.

The compositions of this invention are soothing when applied to oral mucous membranes and may function to relieve minor irritation of the mouth and throat.

A preservative may be added to the compositions of this invention in order to impart an additional guarantee against microbial growth. A preservative may be selected from preservatives known to those of skill in the art, including, but not limited to, one or more of the following: methylparaben, benzoic acid, sorbic acid, gallic acid, propylparaben or the like. The preservative may be present in the compositions of this invention in an amount from about 0.01% to about 0.75% by weight of the composition.

The compositions of this invention may also preferably contain an ester. More preferably, the ester is a fatty acid ester. Most preferably, the ester may include, but is not limited to: isopropyl stearate, isopropyl myristate, isopropyl palmitate, isopropyl laurate and the like. Most preferably, the ester is isopropyl myristate.

The compositions of this invention may contain one or more water-soluble cellulose-derived polymers, gums, chitosans or the like. Such polymers contribute to the viscosity and bioadhesiveness of the compositions of this invention. Preferably, such cellulose-derived polymers are hydroxyalkylcellulose polymers. More preferably, the hydroxyalkylcellulose polymer is hydroxypropylcellulose or Klucel®, available commercially from Hercules Incorporated, Wilmington, Del.

The polyhydric alcohols used in the compositions of this invention are theorized to be useful as warming and heat-generating agents. Antioxidants are useful for preventing oxidation of the composition at elevated temperatures. Honey functions as an insulating agent, protecting the compositions from becoming too cold. The ester, preferably a fatty acid ester, functions as an emollient and lubricant. The cellulose polymer is useful as a viscosity building agent. The compositions of this invention are unique in that they lubricate, warm and soothe the tissues of the user, especially the oral and vaginal mucous membranes, without conveying a feeling of cold. Moreover, they are smooth, lubricating and remain odor-free.

The compositions of this invention may be a liquid, a semi-solid, or a solid depending upon the particular intended use thereof. The compositions of this invention may also be formulated into soft or hard gelatin capsules, suppositories and impregnated into fabrics or polymers.

The compositions of this invention may be used as personal lubricants that convey a feeling of warmth. The feeling of warmth generated by the compositions of this invention is soothing to the skin or mucous membranes where they are applied. The compositions of the invention also possess a sweet and pleasant taste, which is of particular benefit when these compositions are used orally. Such personal lubricants are useful in facilitating sexual intercourse and serve to enhance intimacy in sexual activities.

The compositions of this invention may also be used as personal moisturizers, which convey a feeling of warmth when applied to vaginal or oral mucosa.

The compositions of this invention may also be used as a vehicle to deliver medication or other treatment agents to the biomembranes including, but not limited to, hormones, antimicrobial or antifungal agents and the like. The antifungal agents is preferably an azole or imidazole, including but not limited to, miconazole, econazole, terconazole, sapercona-zole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

Another embodiment of the invention are compositions for vulvovaginal use containing one or more antibiotics. The antibiotic may be chosen from the group including, but not limited to, metronidazole, clindamycin, timidazole, ornidazole, secnidazole, refaximin, trospectomycin, purpuromycin and their pharmaceutically acceptable salts and the like.

Another embodiment of the compositions of this invention include compositions for vulvovaginal use containing one or more antiviral agents. Antiviral agents may preferably include, but are not limited to, immunomodulators, more preferably imiquimod, its derivatives, podofilox, podophyllin, interferon alpha, reticolos, cidofovir, nonoxynol-9 and their pharmaceutically acceptable salts and the like.

Still other embodiments of the compositions of this invention are compositions that include one or more spermicides. The spermicides may preferably include, but are not limited to, nonoxynol-9, octoxynol-9, dodecaethyleneglycol monolaurate, Laureth 10S, and Methoxypolyoxyethyleneglycol 550 Laurate and the like.

Still other embodiments of the compositions of this invention are compositions containing antimicrobial agents. The antimicrobial agents may preferably include, but are not limited to, chlorohexidine gluconate, sodium polystyrene sulfonate, sodium cellulose sulfate, silver particles of micro- and sub-micrometer sizes, silver salts and other antibacterial agents known to the art.

Yet other embodiments of the compositions of this invention are compositions that may include local anesthetics. The local anesthetics may preferably include, but are not limited to, benzocaine, lidocaine, dibucaine, benzyl alcohol, camphor, resorcinol, menthol and diphenylhydramine hydrochloride and the like.

Compositions of the invention may also include plant extracts such as aloe, witch hazel, chamomile, hydrogenated soy oil and colloidal oatmeal, vitamins such as vitamin A, D or E and corticosteroids such as hydrocortisone acetate.

Another embodiment of the compositions and methods of this invention include compositions for vulvovaginal use containing one or more hormones for treating a decrease in estrogen secretion in the woman in need of estrogen replacement such as women with vaginal atrophy. The hormones may preferably include, but are not limited to, estrogen selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, quinestrol and mestranol.

Another embodiment of the compositions and methods of this invention include compositions for vulvovaginal use containing one or more analgesics and/or nonsteroidal anti-inflammatory agents for treating dysmenorrhea or menstrual cramping. The analgesics and nonsteroidal anti-inflammatory agents may preferably include, but are not limited to, aspirin, ibuprofen, indomethacin, phenylbutazone, bromfenac, fenamate, sulindac, nabumetone, ketorolac, and naproxen and the like.

Yet another embodiment of the compositions and methods of this invention includes compositions for oral and vulvovaginal use relates to a method of enhancing the absorption of active agents from the applied compositions into the mucosal membrane by increasing the composition and mucosal tissue temperature via interaction of the polyhydric alcohols in the compositions and moisture on the mucosa and subsequently released heat.

Yet other embodiments of the compositions of this invention include compositions for vulvovaginal use relates to compositions and methods for preventing and/or treating dysmenorrhea by intravaginal warming or heating. Preferably, the composition heats the intravaginal area to a temperature preferably between about 37° C. and about 42° C., more preferably between about 38° C. and about 41° C. The compositions of invention for use in such a method may optionally contain active agents such as analgesics and nonsteroidal anti-inflammatory agents for dysmenorrhea treatment. The composition of the invention may be administered directly into the vagina by an applicator, or be impregnated into vaginal devices such as tampon for intravaginal applications.

The compositions of this invention may be manufactured as a coating of a tampon, or dispersing throughout the absorbent tampon material, or enclosed inside as a core of a tampon. The compositions of this invention for the warming tampon for preventing and/or treating dysmenorrhea preferably include a mixture of polyethylene glycols of various molecular weights produced by The Dow Chemical Company (Midland, Mich.) under the trade names of CARBOWAX SENTRY PEG 300 NF, CARBOWAX SENTRY PEG 400 NF, CARBOWAX SENTRY PEG 600 NF, CARBOWAX SENTRY PEG 900 NF, CARBOWAX SENTRY PEG 1000 NF, CARBOWAX SENTRY PEG 1450 NF, CARBOWAX SENTRY PEG 3500 NF, CARBOWAX SENTRY PEG 4000 NF, CARBOWAX SENTRY PEG 4600 NF, and CARBOWAX SENTRY PEG 8000 NF. The compositions of this invention for dysmenorrhea prophylaxis and treatment may contain one or more water-soluble cellulose-derived polymers and gums that form gels around the polyhydric alcohols such as glycerin, propylene glycol and polyethylene glycols thus reducing the dissolution of the polyhydric alcohols, prolonging the salvation heat release, and regulating the elevated temperature in the preferred temperature range.

Table 1 lists warming personal lubricant compositions that contain a combination of polyethylene glycol and propylene glycol. We have found that such compositions, containing propylene glycol and one or more polyethylene glycols have developed a distinctive odor over time, especially when these were stored at higher temperatures. The odor development was especially associated with compositions containing polyethylene glycol 400 and propylene glycol combination.

TABLE 1

| Ingredient % w/w | Composition 1 | Composition 2 | Composition 3 | Composition 4 |
|---|---|---|---|---|
| Propylene Glycol | 74.40 | 73.55 | 74.77 | 74.95 |
| Polyethylene Glycol 400 | 25.00 | 25.00 | 25.00 | 25.00 |
| Gelling Agent | 0.40 | 1.25 | 0.03 | — |
| Lactic Acid | 0.20 | 0.20 | 0.20 | — |
| BHT | — | — | — | 0.05 |

The odor was initially detected in the volatile components in the compositions that partitioned into the gas phase in the headspace of packages containing those compositions. To identify the odor components, the gas phase in the headspace was analyzed by the Purge & Trap-Thermal Desorption-GC-MS. GC-MS results showed significantly higher concentration of propanal, acetone, acetaldehyde, ethanol, isopropanol and cyclic acetal and ketal derivatives of these compounds with propylene glycol. These odor-causing chemicals were also found in the product samples, although in much lower concentrations.

The GC-MS study indicated that the formulations under investigation were undergoing oxidative degradation, when stored at elevated temperature.

Although antioxidants have been known in the art for their role in preventing oxidation in oils and oil based emulsions, their use in warming personal lubricant compositions is new. Moreover, certain previously-known antioxidants have been utilized in the past to prevent oxidation reactions resulting in change of color or discoloration of the products. Substantial prevention of odor production in polyhydric alcohol compositions, however, is new. We found, surprisingly, that certain antioxidants were capable of remediating odor formation in the propylene glycol/polyethylene glycol compositions of this invention whereas other antioxidants were ineffective in accomplishing this result.

Accordingly, antioxidants were added to compositions according to this invention and are set forth in Table 2. These compositions were subjected to increased temperatures ranging from 5° C. to 60° C. for a period of 8 days to 12 weeks and were subjectively evaluated for development of odor by comparing compositions containing antioxidants with control samples of the compositions without any antioxidants.

TABLE 2

Warming Compositions With and Without Antioxidants

| | FORMULATIONS | | |
|---|---|---|---|
| INGREDIENTS | w/0.05% BHT | w/0.1% BHA | w/o antioxidant (control) |
| Propylene Glycol | 74.35 | 74.3 | 74.4 |
| Polyethylene Glycol 400 | 25 | 25 | 25 |
| Lactic Acid | 0.2 | 0.2 | 0.2 |
| Gelling Agent | 0.40 | 0.40 | 0.40 |
| BHT | 0.05 | — | — |
| BHT | — | 0.1 | — |
| Total | 100.00 | 100.00 | 100.00 |

After incubation for eight (8) days at 60° C., we observed that the compositions containing 0.05% BHT and 0.1% BHA did not product any odor while the control composition without antioxidants developed a strong odor.

Compositions 1-3 set forth in Table 1 contain the combination of propylene glycol and PEG 400 that we theorize causes the formation of odor in such compositions. As Composition 4 of Table 1 contains propylene glycol and PEG 400 without a gelling agent or lactic acid, we determined to study this product as a test formulation to screen antioxidant candidates. Once an effective antioxidant candidate was selected, we added it to Compositions 1-3 set forth in Table 1. Preferably, the compositions of this invention contain one or more antioxidants in an amount of from about 0.01% w/w to about 1% w/w. More preferably, they contain from about 0.01% w/w to about 0.5% w/w. Most preferably, they contain from about 0.01% w/w to about 0.1% w/w. Potential candidates for use as antioxidants are set forth in Table 3 below.

TABLE 3

Potential Antioxidants and Usage Level

| Antioxidants | Usage level (w/w) |
|---|---|
| dl-alpha-Tocopherol | 0.1% |
| Ascorbic acid | 0.05% |
| Ascorbyl Palmitate | 0.015% |
| BHT | 0.01% |
| Propyl Gallate | 0.05% |
| t-Butyl Hydroquinone (TBHQ) | 0.01% |

Several of the foregoing antioxidants were added to the warming composition according to this invention containing 75%/25% propylene glycol/PEG 400. The warming compositions containing the antioxidants set forth in Table 3 were stored at 5, 25, 40 and 60° C. These samples were removed after 2, 4, or 6 weeks, followed by subjective evaluation of the odor. The antioxidants listed above in Table 3 were dissolved in the warming formulation either by heating or increasing the mixing speed to obtain a clear solution.

We found that propyl gallate and TBHQ resulted in a color change in the compositions from colorless to yellowish/brown quickly, within a week at 40° C. and 60° C. Thus, we determined that these two antioxidants would not be suitable candidates for use as antioxidants in the compositions of this invention.

Compositions containing alpha-tocopherol, ascorbic acid, ascorbyl palmitate and BHT (0.01%) were evaluated for odor development up to 6 weeks at elevated temperatures of 5, 25, 40 and 60° C. The control composition, without antioxidants, was also evaluated. The results of this evaluation are set forth below in Table 4.

TABLE 4

| Description | Temperature (° C.) | 2 weeks | 4 weeks | 6 weeks |
|---|---|---|---|---|
| 0.1% a-Tocopherol | 5 | ND | No off-odor | No off-odor |
|  | 25 | ND | ND | No off-odor |
|  | 40 | ND | Little odor or no odor | No odor/slight odor |
|  | 60 | ND | Solvent odor in the beginning | Slight odor |
| 0.01% BHT | 5 | No off-odor | No off-odor | No off-odor |
|  | 25 | ND | No off-odor | No off-odor |
|  | 40 | No off-odor | Slight odor | No off-odor |
|  | 60 | No off-odor | Odor in the beginning | No odor from bottle; moderate odor in jar |
| 0.05% Ascorbic acid/ | 5 | ND | No off-odor | No off-odor |
|  | 25 | ND | ND | Slight odor or no odor |
|  | 40 | ND | Slight odor | Slight odor |
|  | 60 | ND | Solvent odor in the beginning | Strong odor |
| 0.015% Ascorbyl Palmitate | 5 | ND | No off-odor | No off-odor |
|  | 25 | ND | ND | No off-odor |
|  | 40 | ND | Slight odor | Slight odor or no odor |
|  | 60 | ND | Solvent odor in the beginning | Strong odor |
| Control (75/25 Propylene glycol/ PEG 400) | 5 | No off-odor | ND | No off-odor |
|  | 25 | ND | ND | Very slight odor |
|  | 40 | No off-odor | ND | Slight odor |
|  | 60 | Strong odor | Strong odor | Strong odor |

ND: Not determined.

Table 4 summarizes the results of odor development and demonstrates that compositions having no antioxidant developed strong odor after 2 weeks at 60° C. At lower temperatures (5-40° C.), only slight odor was noticeable after 6 weeks. Alpha-tocopherol and 0.01% BHT was most effective in controlling the odor in the compositions of this invention. After 6 weeks, only slight odor or no odor was found at 60° C. By contrast, formulations containing ascorbic acid or ascorbyl palmitate, developed strong odor after 6 weeks at of 60° C.

Compositions according to this invention containing antioxidants and the control composition were further compared and rated subjectively, as set forth below in Table 5. After storage at 60° C. for 4-6 weeks, the odor in the composition containing alpha-tocopherol or 0.01% BHT had the lowest odor scores. The composition containing ascorbyl palmitate produced the strongest odor, as compared with the other compositions. This indicates that ascorbyl palmitate is relatively ineffective as an antioxidant in the compositions of this invention. Ascorbic acid, at 0.05%, showed some effectiveness, however.

TABLE 5

| Description | Duration | Container | Average Rating |
|---|---|---|---|
| 0.1% Tocopherol | 5 weeks | Spray bottle | 1 |
| 0.015% Ascorbyl palmitate | 5 weeks | Spray bottle | 5 |
| 0.05% Ascorbic acid | 5 weeks | Spray bottle | 2.5 |
| 0.01% BHT | 6 weeks | Spray bottle | 1 |
| Control (no antioxidant) | 4 weeks | Glass jar/vial | 4 |

Rating scale: 1-5; 1 has least odor and 5 has strongest odor.

Combinations of antioxidants were also evaluated, as summarized in Table 6. The compositions containing the combinations of antioxidants as set forth above were stored at temperatures of 5, 25, 40 and 60° C. and tested for odor production at two weeks and six weeks. The results of odor evaluation for these antioxidant combinations are summarized in Table 7 below. The data set forth in Table 7 demonstrates that combinations of antioxidants may be useful in the compositions of this invention and permit the use of lower levels of the antioxidants in order to achieve a substantial prevention of the production of odor in the compositions of this invention. Antioxidant levels may be reduced by approximately 25% to about 50% and still achieve a relatively odorless resulting composition.

TABLE 6

| Antioxidants combinations | Usage level (w/w) |
|---|---|
| dl-alpha-Tocopherol/BHT | 0.05%/0.005% |
| dl-alpha-Tocopherol/Ascorbic acid | 0.05%/0.025% |
| Ascorbic acid/BHT | 0.025%/0.005% |
| Other preferred ranges include the following: | |
| dl-alpha-Tocopherol/BHT | 0.05%/0.005% (0.01-0.15%/0.001-0.01%) |
| dl-alpha-Tocopherol/Ascorbic acid | 0.05%/0.025% (0.01-0.15%/0.025-0.10%) |
| Ascorbic acid/BHT | 0.025%/0.005% (0.025-0.1%/0.001-0.01%) |

TABLE 7

| Description | Temperature (° C.) | 2 weeks | 6 weeks |
|---|---|---|---|
| Ascorbic acid + BHT | 5 | No odor | ND |
|  | 25 | ND | No odor |
|  | 40 | No odor | Slight odor |
|  | 60 | Slight odor | Slight odor |

TABLE 7-continued

| Description | Temperature (° C.) | 2 weeks | 6 weeks |
|---|---|---|---|
| Tocopherol + Ascorbic acid | 5 | Very slight odor | No odor |
| | 25 | ND | No odor |
| | 40 | Slight odor | No odor |
| | 60 | Slight odor | No odor or slight odor |
| Tocopherol + BHT | 5 | No odor | No odor |
| | 25 | ND | No odor |
| | 40 | Slight odor | Slight odor |
| | 60 | Slight odor | Slight odor |

ND: not determined.

Thus, one or more selected antioxidants may be useful in the compositions of this invention to work to prevent odor formation over time while the compositions are being stored at ambient or elevated temperature.

What is claimed is:

1. A substantially anhydrous lubricant composition comprising at least one polyhydric alcohol, a bioadhesive agent and at least one antioxidant, wherein said antioxidant is selected from the group consisting of tocopherol and butylated hydroxytoluene, (BHT) and combinations thereof; and wherein said compositions are substantially odor-free when stored at 40° C. for at least two weeks.

2. A substantially anhydrous lubricant composition according to claim 1, wherein said antioxidant is dl-alpha-tocopherol.

3. A substantially anhydrous lubricant composition according to claim 1, wherein said antioxidant is BHT.

4. A substantially anhydrous lubricant composition according to claim 1, wherein said antioxidant is a combination ascorbic acid and BHT.

5. A substantially anhydrous lubricant composition according to claim 1, wherein said composition does not develop odor when stored at 60° C. for at least six weeks.

6. A substantially anhydrous lubricant composition comprising at least one polyhydric alcohol, a bioadhesive agent and at least one antioxidant selected from the group consisting of tocopherol and butylated hydroxytoluene (BHT) and combinations thereof, wherein said polyhydric alcohol is selected from the group consisting of propylene glycol, polyethylene glycol, butylethylene glycol, hexylene glycol and combination thereof; and wherein said composition does not develop odor when stored at 40° C. for at least two weeks.

7. A substantially anhydrous lubricant composition according to claim 6, where the said polyhydric alcohol is propylene glycol.

8. A substantially anhydrous lubricant composition according to claim 6, where the said polyhydric alcohol is butylethylene glycol.

9. A substantially anhydrous lubricant composition according to claim 6, where the said polyhydric alcohol is hexylene glycol.

10. A substantially anhydrous lubricant composition according to claim 6, wherein said composition does not develop odor when stored at ambient room temperature (60.degree. C.) for at least for one year.

11. A substantially anhydrous lubricant composition comprising propylene glycol, a polyethylene glycol and an antioxidant selected from the group consisting of tocopherol and butylated hydroxytoluene (BHT) and combinations thereof, wherein said composition does not develop odor when stored 40° C. for at least two weeks.

12. A substantially anhydrous lubricant composition comprising at least one polyhydric alcohol, a bioadhesive agent and at least one antioxidant, wherein said antioxidant is selected from the group consisting of tocopherol and butylated hydroxytoluene, (BHT) and combinations thereof and wherein said composition does not develop odor when stored at 40° C. for at least two weeks.

13. A substantially anhydrous lubricant composition comprising at least one polyhydric alcohol, a bioadhesive agent and at least one antioxidant, wherein said antioxidant is selected from the group consisting of tocopherol and butylated hydroxytoluene, (BHT) and combination thereof and wherein said composition does not develop odor when stored at 40° C. for at least two weeks.

* * * * *